United States Patent [19]

VandenBerg

[11] Patent Number: Plant 6,498

[45] Date of Patent: Dec. 27, 1988

[54] CHRYSANTHEMUM PLANT NAMED AKIRA

[75] Inventor: Cornelis P. VandenBerg, Salinas, Calif.

[73] Assignee: Yoder Brothers, Inc., Barberton, Ohio

[21] Appl. No.: 49,831

[22] Filed: May 15, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Akira particularly characterized by its flat capitulum form; spoon daisy capitulum type; red-purple ray floret color; diameter across face of capitulum of up to 15 cm at maturity when grown as a pinched disbudded pot mum; uniform eight week photoperiodic flowering response to short days; medium plant height when grown as a pinched pot mum; recommended both as disbudded and spray pot mum; spreading and prolific branching pattern.

3 Drawing Sheets

The present invention comprises a new and distinct cultivar of Chrysanthemum, botanically known as *Chrysanthemum morifolium,* Ramat., and referred to by the cultivar name Akira.

Akira, identified as 82349004, was originated from a cross made by Cornelis P. VandenBerg in a controlled breeding program in Salinas, Calif., in 1982.

The female parent of Akira was an unnamed seedling identified as 81C48001. The male parent of Akira was an unnamed seedling identified as 81C53001.

Akira was discovered and selected as one flowering plant within the progeny of the stated cross by Cornelis P. VandenBerg in December of 1982, in a controlled environment in Salinas, Calif.

The first act of asexual reproduction of Akira was accomplished when vegetative cuttings were taken from the initial selection in March of 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Akira are firmly fixed and are retained through successive generations of asexual reproduction.

Akira has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Akira, which, in combination, distinguish this Chrysanthemum as a new and distinct cultivar:

1. Flat capitulum form.
2. Spoon daisy capitulum type.
3. Red-purple ray floret color.
4. Diameter across face of capitulum up to 15 cm at maturity when grown as a pinched disbudded pot mum.
5. Uniform eight week photoperiodic flowering response to short days.

6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Branching pattern is spreading and prolific.

The accompanying photographic drawings show typical inflorescence and leaf characteristics of Akira, with the colors being as nearly true as possible with illustrations of this type. Sheet 1 is a color photograph of Akira grown as a pinched disbudded pot mum. Sheet 2 is a black and white photograph of three views of the inflorescence of Akira. Sheet 3 is a black and white photograph showing the upper and under sides of the leaves of Akira at three stages of development (mature, intermediate and immature).

Of the commercial cultivars known to the inventor, the most similar in comparison to Akira is Neoga, disclosed in a pending plant patent application of applicant.

Reference is made to attached Chart A, which compares certain characteristics of Akira to the same characteristics of Neoga.

Similar traits are capitulum form and type, branching pattern, plant height, flowering response, and recommended use. Akira has a red-purple ray floret color, compared with the purple ray floret color of Neoga. Also, Akira has a larger capitulum diameter than Neoga.

In the following description color references are made to the Royal Horticultural Society Colour Chart. The color values were determined on plant material grown as a pinched disbudded pot mum in Salinas, Calif. on Dec. 12, 1986.

Classification:

*Botanical.*—*Chrysanthemum morifolium,* Ramat., cv Akira.

*Commercial.*—Spoon daisy disbud and spray pot mum.

INFLORESCENCE a. Capitulum:

*Form.*—Flat.

*Type.*—Spoon daisy.

*Diameter across face.*—Up to 15 cm at maturity.

B. Corolla of ray florets:

*Color (general tonality from a distance of three meters).*—Red-purple.

*Color (upper surface of spoon tips).*—70A to 70B.

*Color (tubes).*—78C to 78D.

*Shape.*—Base tubular. Distal portion open, flattened and spoon like. Ray florets in each capitulum range from completely tubular to approximately 50% of the length of the ray floret flattened and spoon like.

C. Corolla of disc florets:

*Color (mature).*—9A to 9B.

*Color (immature).*—144B.

D. Reproductive organs:

*Androecium.*—Present in disc florets only; no pollen.

*Gynoecium.*—Present in both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Deeply lobed and serrated.

CHART A

Comparison of AKIRA and NEOGA

| CULTIVAR | RAY FLORET COLOR | CAPITULUM FORM & TYPE | BRANCHING PATTERN |
|---|---|---|---|
| AKIRA | RED PURPLE | SPOON DAISY | SPREADING |
| NEOGA | PURPLE | SPOON DAISY | SPREADING |

| CULTIVAR | DIAMETER ACROSS FACE OF CAPITULUM | PLANT HEIGHT | FLOWERING RESPONSE PERIOD | RECOMMENDED USE |
|---|---|---|---|---|
| AKIRA | Up to 15 cm AS DISBUDDED POT MUM | MEDIUM | 8 WEEK | DISBUD and SPRAY |
| NEOGA | Up to 12 cm AS DISBUDDED POT MUM | MEDIUM | 8 WEEK | DISBUD and SPRAY |

COMPARISONS MADE OF PLANTS GROWN AS PINCHED POT MUM IN SALINAS, CALIFORNIA AND LEAMINGTON, CANADA

I claim:

1. A new and distinct Chrysanthemum plant named Akira, as described and illustrated, and particularly characterized as to uniqueness by the combined characteristics of flat capitulum form; spoon daisy capitulum type; red-purple ray floret color; diameter across face of capitulum of up to 15 cm at maturity when grown as a pinched disbudded pot mum; uniform eight week photoperiodic flowering response to short days; medium plant height when grown as a pinched pot mum; recommended both as disbudded and spray pot mum; and spreading and prolific branching pattern.

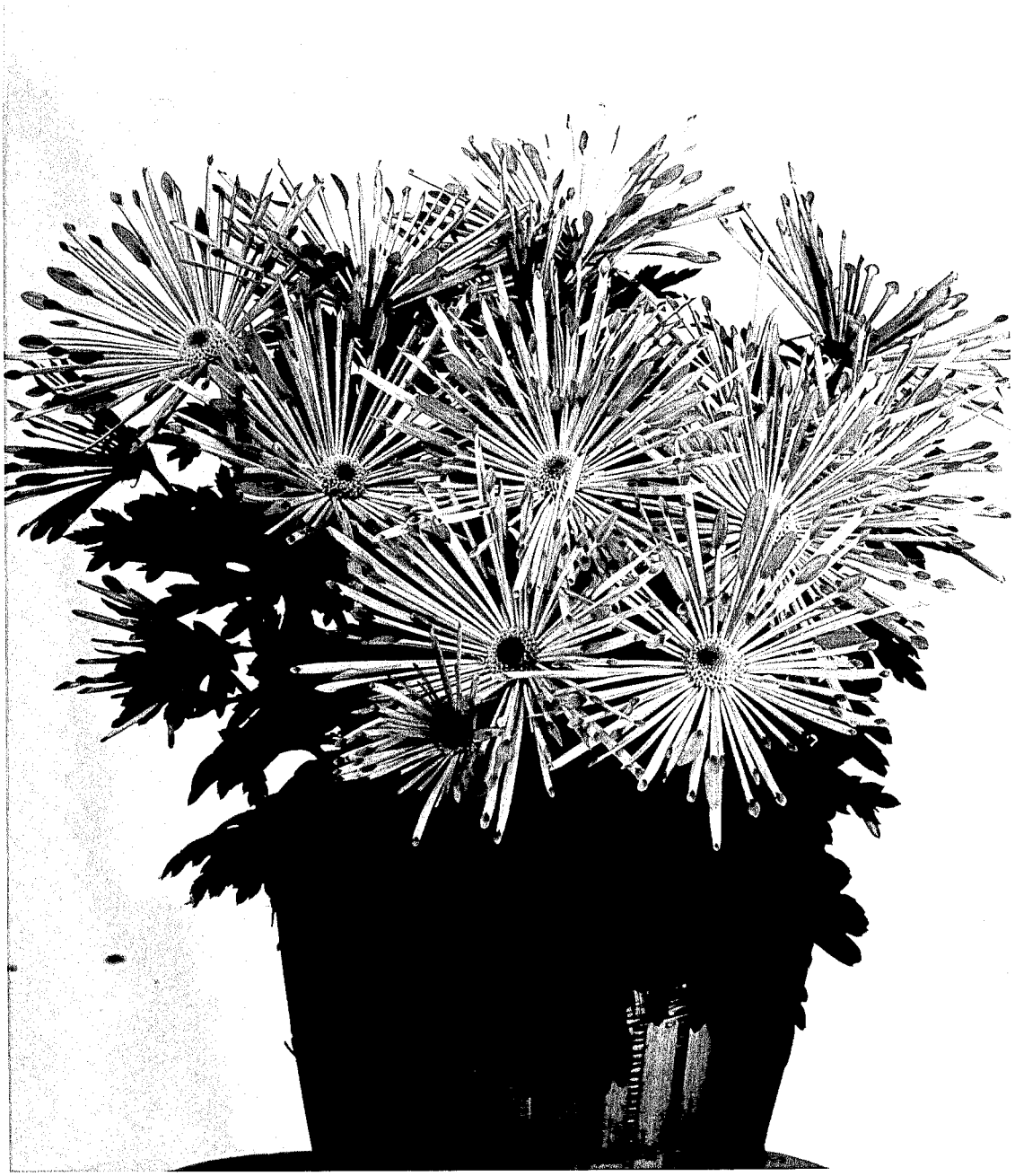

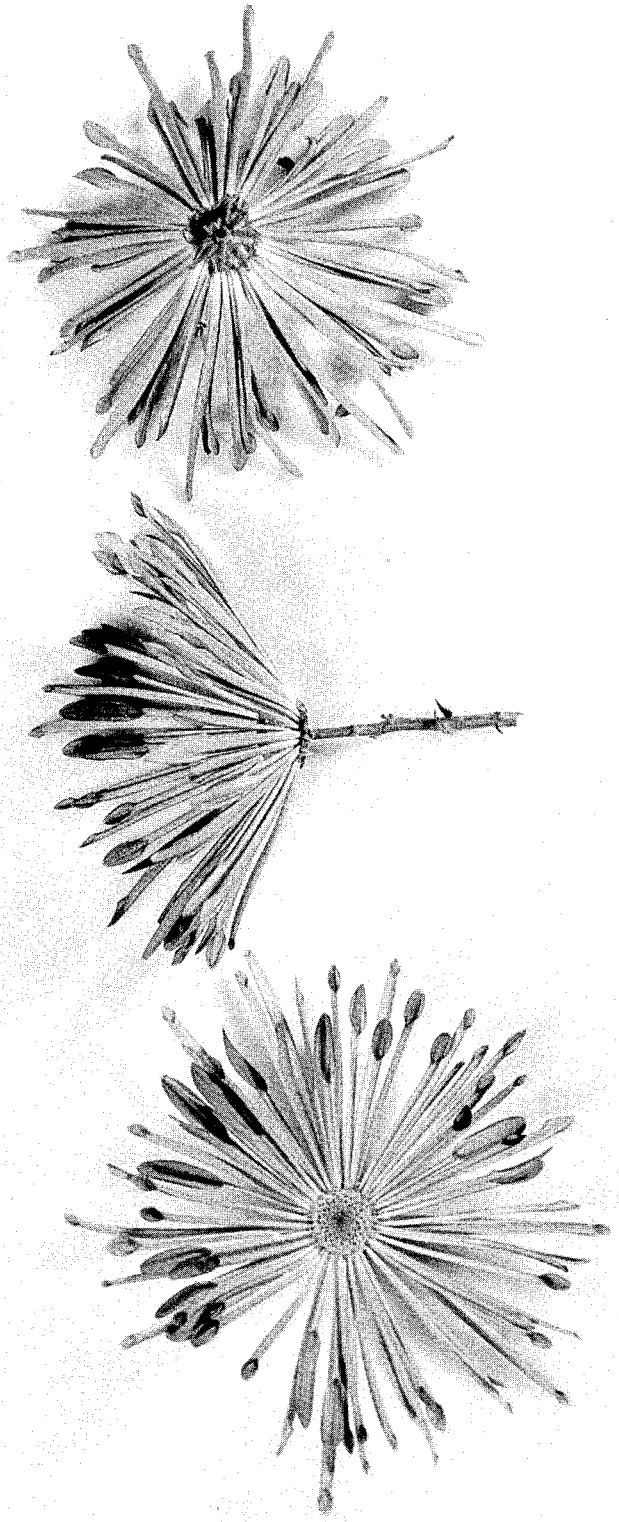

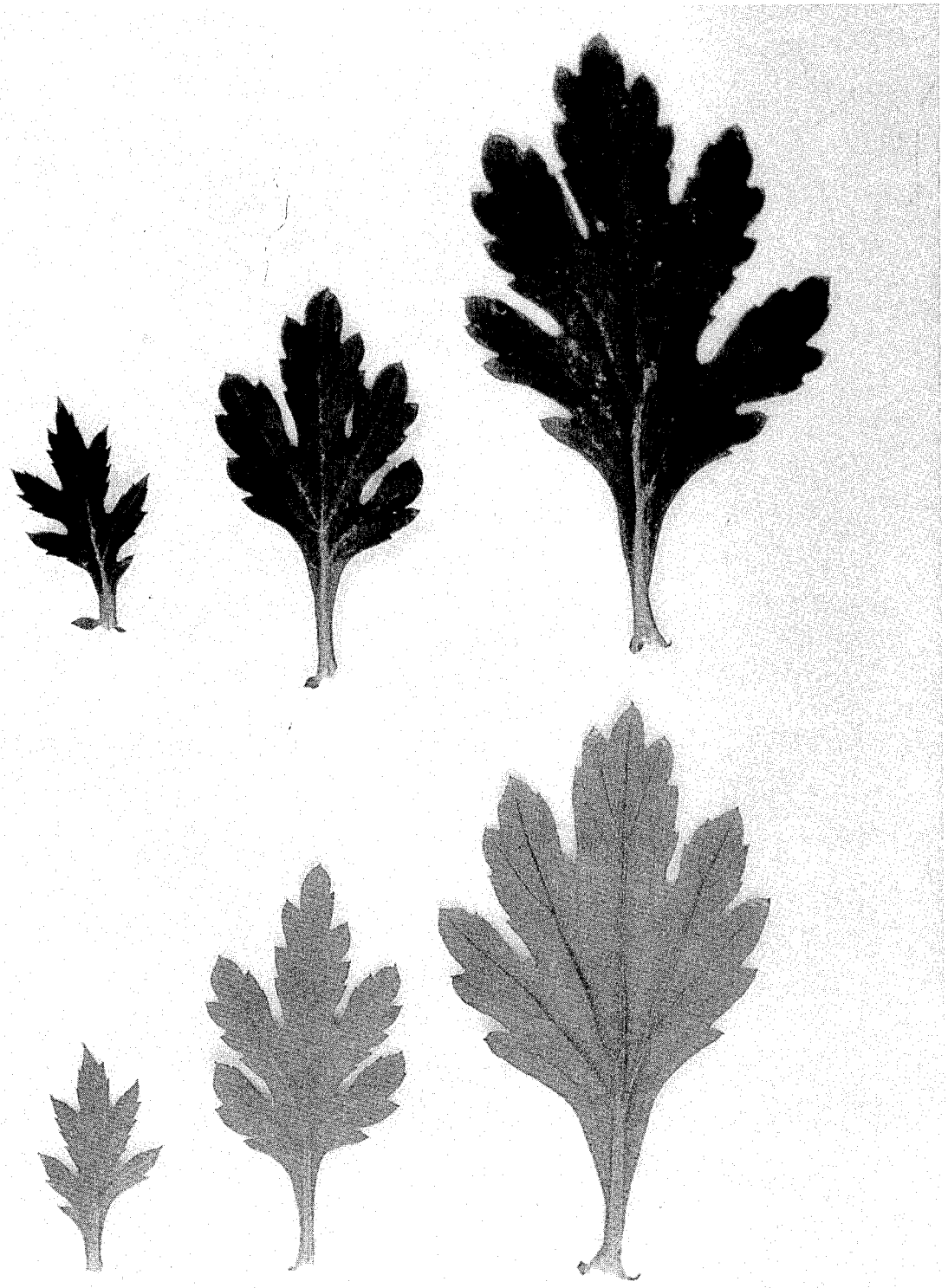

* * * * *